United States Patent
Tepic

(10) Patent No.: US 8,968,368 B2
(45) Date of Patent: Mar. 3, 2015

(54) PLATE AND SCREWS FOR TREATMENT OF BONE FRACTURES

(75) Inventor: Slobodan Tepic, Zurich (CH)

(73) Assignee: Kyon, Zurich (CH)

( * ) Notice: Subject to any disclaimer, the term of this patent is extended or adjusted under 35 U.S.C. 154(b) by 948 days.

(21) Appl. No.: 11/816,668

(22) PCT Filed: Feb. 17, 2006

(86) PCT No.: PCT/EP2006/001473
§ 371 (c)(1),
(2), (4) Date: Aug. 20, 2007

(87) PCT Pub. No.: WO2006/089695
PCT Pub. Date: Aug. 31, 2006

(65) Prior Publication Data
US 2008/0200955 A1    Aug. 21, 2008

(30) Foreign Application Priority Data
Feb. 22, 2005  (EP) ..................................... 05003773

(51) Int. Cl.
*A61B 17/80*    (2006.01)
*A61B 17/86*    (2006.01)

(52) U.S. Cl.
CPC ............. *A61B 17/80* (2013.01); *A61B 17/8085* (2013.01); *A61B 17/8625* (2013.01)
USPC ..................................................... 606/280

(58) Field of Classification Search
USPC ................... 606/280, 283, 284, 285, 291, 295
See application file for complete search history.

(56) References Cited

U.S. PATENT DOCUMENTS

| | | | | |
|---|---|---|---|---|
| 3,534,731 A * | 10/1970 | Muller | ......................... | 606/105 |
| 3,695,259 A * | 10/1972 | Yost | .............................. | 606/288 |
| 4,219,015 A * | 8/1980 | Steinemann | ................... | 606/280 |
| 4,696,290 A * | 9/1987 | Steffee | .......................... | 606/286 |
| 4,838,252 A * | 6/1989 | Klaue | ............................ | 606/280 |
| 5,002,544 A * | 3/1991 | Klaue et al. | ................... | 606/280 |
| 5,053,036 A * | 10/1991 | Perren et al. | .................. | 606/291 |
| 5,269,784 A * | 12/1993 | Mast | ............................. | 606/288 |
| 5,474,553 A * | 12/1995 | Baumgart | ....................... | 606/71 |
| 5,549,612 A * | 8/1996 | Yapp et al. | .................... | 606/293 |
| 5,702,396 A | 12/1997 | Hoenig et al. | | |
| 5,709,686 A * | 1/1998 | Talos et al. | .................... | 606/281 |
| 5,733,287 A * | 3/1998 | Tepic et al. | ................... | 606/280 |

(Continued)

FOREIGN PATENT DOCUMENTS

EP    0 518 079 A    12/1992
EP    1 348 390 A    10/2003

(Continued)

*Primary Examiner* — Christian Sevilla
(74) *Attorney, Agent, or Firm* — Rothwell, Figg, Ernst & Manbeck, P.C.

(57) ABSTRACT

A plate for treatment of bone fractures with reduced potential contact to bone through a combination of annular recesses surrounding the screw holes at the lower, bone facing surface of the plate and transverse grooves between the holes, allows for use of locking as well as conventional bone screws. With the transverse grooves cut into the plate from the lower side, as well as from the sides, the strength of the plate at the span between the holes is lower than at the screw holes. The plate can be bent in both planes without undue deformation of the screw holes. Protection of the holes during bending is afforded by hole plugs, which may be provided pre-installed in order to reduce surgery time. Screw hole plugs may then be left in place in the holes not used for bone screws.

21 Claims, 9 Drawing Sheets

(56) References Cited

U.S. PATENT DOCUMENTS

| | | | |
|---|---|---|---|
| 6,017,345 A | | 1/2000 | Richelsoph et al. |
| 6,093,201 A * | | 7/2000 | Cooper et al. ............... 606/232 |
| 6,123,709 A * | | 9/2000 | Jones ........................... 606/281 |
| 6,129,730 A * | | 10/2000 | Bono et al. ................... 606/291 |
| 6,309,393 B1 * | | 10/2001 | Tepic et al. ................... 606/280 |
| 8,246,664 B2 * | | 8/2012 | Terrill et al. .................. 606/286 |
| 8,491,643 B2 * | | 7/2013 | Lauryssen et al. ............ 606/280 |
| 2002/0058940 A1 * | | 5/2002 | Frigg et al. ..................... 606/69 |
| 2004/0039387 A1 * | | 2/2004 | Gause et al. ................... 606/69 |
| 2004/0097937 A1 * | | 5/2004 | Pike et al. ...................... 606/69 |
| 2004/0102775 A1 * | | 5/2004 | Huebner ........................ 606/69 |
| 2004/0177847 A1 * | | 9/2004 | Foley et al. .................. 128/95.1 |
| 2006/0264946 A1 * | | 11/2006 | Young ............................ 606/69 |

FOREIGN PATENT DOCUMENTS

| | | | | |
|---|---|---|---|---|
| EP | 1348390 A2 * | 10/2003 | ............ | A61B 17/80 |
| JP | 3099430 U | 11/2003 | | |
| WO | WO 99/38447 A | 8/1999 | | |

* cited by examiner

A-A

A-A

B-B

VIEW A

VIEW B

PLATE AND SCREWS FOR TREATMENT OF BONE FRACTURES

CROSS REFERENCE TO RELATED APPLICATION

This application is a 35 USC §371 National Phase Entry Application from PCT/EP2006/001473, filed Feb. 17, 2006, and designating the United States.

This invention relates to plates and screws for internal fixation of bone fractures. Geometry of the plate and in particular the lower, bone-facing, surface of the plate is at the core of the invention. It leads to a large reduction of the potential contact between the plate and the bone, hence minimizing the damage done to the bone vascular supply by plating itself. Furthermore, the plate screw holes are shaped to allow use of either conventional (ISO standardized) or the special, locking screws. These goals are achieved without compromising mechanical properties of the plate and the plate-bone construct.

BACKGROUND

Healing of fractured bones treated by internal fixation depends on blood supply, which is provided to bone by both endosteal and periosteal routes. Both can be damaged in the fracture event, but also later, by the treatment. Conventional plates present a particularly high risk to the periosteal blood supply since they are made to fit the bone as closely as possible and then screwed tightly onto the bone. This kills the periosteum, and the bone, which needs it for its blood supply. Dead bone cannot heal and it presents a particularly high risk of infection. Through remodelling, bone can be restored, but seldom to its original shape and mechanical properties.

Many different plates, which reduce the area of contact to the bone, have been introduced to clinical use during the past two decades. Related to these developments are also different solutions to stably connect, or lock, bone screws and the plates. As the contact between the plate and the bone is reduced to very small areas, locking the screws becomes imperative—conventional screws, which are anchored in bone and compress the plate to the bone could produce contact pressures in excess of bone compressive strength. This would compromise stability of the construct and hence the process of fracture healing.

PRIOR ART

U.S. Pat. No. 3,552,389, Aligower, et al, discloses a so-called compression plate, or dynamic compression plate, which has become de facto standard in internal fixation of bone fractures. Screws in this plate can be used to cause an axial displacement between the plate and the bone segment, resulting in compression of the bone segments at the fracture. The main drawback of these, now generic, plates is the extensive contact between the plate and the bone and consequently demolition of the periosteal blood supply.

U.S. Pat. No. 4,484,570, Sutter, teaches how to lock the screws in so-called mandibular, reconstruction plates. This invention has modified many of the later and current efforts to improve the plating.

U.S. Pat. No. 4,838,252, Klaue, discloses a bone plate of a trapezoidal shape, narrower at the side facing the bone. The intent is to reduce the contact, but stability is compromised, especially in torsion.

U.S. Pat. No. 5,002,544, Klaue, discloses a trapezoidal shape of the plate, combined with transverse under cuts aimed at further reducing the contact to the bone.

U.S. Pat. No. 5,053,036, Perren, et al, teaches how to shape the lower surface of the plate using a longitudinal arch-shaped cut, and a plurality of side openings, or transverse cuts.

U.S. Pat. No. 5,151,103, Tepic et al, discloses a solution to locking screws into the plates via friction-based, self-locking mechanism.

U.S. Pat. No. 5,269,7841, Mast, teaches how to lock the screw with the plate using a nut, placed between the plate and the bone.

U.S. Pat. No. 5,709,686, Talos, Schmoker, discloses an elongated screw hole with threads on the sidewalls, allowing for locking of the screw.

U.S. Pat. No. 5,733,287, Tepic, Bresina, teaches how to reduce stress concentration around the screw holes. There is no teaching of recesses surrounding the screw holes on the bone-facing side of the plate.

U.S. Pat. No. 5,741,258, Klaue, Mast, teaches another concept of a locking nut for fixing the screw to the plate.

U.S. Pat. No. 5,810,823, Klaue, Mast, teaches how to design a plate with very small contact to the bone, centred on the screw. This, again, compromises stability, especially against torsion.

U.S. Pat. No. 6,206,881, Frigg, Schavan, teaches how to lock the screws into a plate of lesser hardness.

U.S. Pat. No. 6,602,255, Campbell, Harrington, teaches a locking mechanism for screws and plates with a third body (spring) element.

US Pat. Appl. 20020045901, Wagner, Frigg, discloses an elongated screw hole designed to accept either a standard, or a locking screw.

U.S. Pat. No. 6,017,345 discloses a bone fixation plate assembly having a number of apertures (24) wherein the bore or aperture can include at least one internal annular recess (13) on either surface.

EP 348 390 A2 discloses a bone plate system comprising a bone plate which has apertures and transverse grooves which are not positioned between the apertures.

SUMMARY OF THE INVENTION

The present invention relates to a plate for treating bone fractures, having an upper surface, a lower surface, and at least two preferably circular holes, extending from the upper surface to the lower surface, whereby said holes are surrounded with recesses at the lower, essentially planar, surface.

The purpose of the recess is to eliminate the potential contact of the plate and the bone surrounding the screw. The lower surface of the plate is essentially planar.

Said recesses are preferably of approximately annular form. While the shape of the recess may be circular in shape when viewed from the lower side of the plate, other shapes can be used to achieve the same effect. A shape somewhat elongated in the direction of the long axis of the plate can be used to reduce the stresses at the transverse aspect of the plate along the remaining lower surface. The recess can also be rounded at its base and/or faceted at its edge as one skilled in art would do to avoid stress concentrations at sharp corners, or injuries at sharp edges.

Preferably, the plate width is larger, preferably approximately 2.5 to 3.5 times larger than the diameter of said holes; and the diameter of said recesses is preferably larger, preferably approximately 1.5 to 2 times larger than the diameter of said holes.

The depth of the recess should be scaled to the thickness of the plate; a good compromise between the need to provide a safe clearance to the bone and the need to maintain sufficient strength of the plate suggests a preferred ratio of about 1 to 4, i.e. the depth of the recess should be about 25% of the plate thickness. In general, the depth of the recess may be about 20 to about 30% of the plate thickness. In one preferred embodiment, the depth of the recesses is therefore approximately one fourth of the plate thickness.

The plate preferably comprises transverse grooves. In a preferred embodiment, the transverse grooves are positioned between at least some of the holes to further reduce the potential contact of the lower surface of the plate and the bone, leaving intact only two small areas of the original, essentially planar lower surface per said hole.

Preferably, the transverse grooves are positioned between at least some of the holes, preferably on the lower, bone facing side of the plate. Transverse grooves may also be present on the upper side of the plate. Preferably, there is one or more transverse groove between any two holes. Transverse grooves may also be cut into the plate from the sides, or the sides may comprise side cuts which reduce the width of the plate between the holes.

In a preferred embodiment of the present invention, the transverse groove spans the area between the recesses between two holes, and even more preferably, the transverse groove overlaps with part of the recess around the hole. This way, the plate can be designed so that the areas of the lower, bone facing side of the plate, which are not covered by transverse grooves, are very small areas. This ensures that only those small areas will contact the bone when the plate is in place. It is also possible that the transverse grooves are positioned so that they are essentially adjacent. In this case, the areas remaining for bone contact are very small or consist only of an edge. Preferably, the area remaining for bone contact has about the width of the hole.

The depth of the transverse grooves is preferably about the same as the depth of the recesses. Preferably, the depth of the transverse grooves is equal or larger than the depth of the recesses. Further, the depth of the transverse grooves may also be slightly larger than the depth of the recesses. Alternatively, the depth of the transverse grooves may also be slightly smaller than the depth of the recesses.

In a preferred embodiment, the hole in its upper section adjacent to the upper surface is conical in shape. The conical section of the hole preferably has a cone angle above the self-locking range, preferably 30 degrees or more.

The mid-to-lower section of the hole is preferably provided with threads.

The plate of the present invention may further be provided with angular release cuts, extending longitudinal aspect of the hole in its mid-to-lower section.

The geometry of said plate may further be modified by side cuts, spaced between at least some of the holes. In many uses of bone plates, it is desirable to bend the plate in both planes. So-called reconstruction plates with deep side cuts do exist, but those are intended for use in less loaded, complex bones, e.g. those of the pelvis. The plate disclosed in the present invention may be provided with side cuts which allow for sufficient bending of the plate in both planes to match the shapes of the long bones, especially near joints. An important, further function of the side cuts is to make the strength of the plate more uniform. This is beneficial not only for added ease of adaptation, but also for reducing the risk of plate breakage in functional use.

The cross section between the holes preferably has lower moments of resistance than the cross section at the holes.

The screw holes can be plugged by plugs which, basically, are just short locking screws. Using such plugs in the plate holes, while adapting the plate to the bone by bending and torsion, reduces the risk of excessive deformation of the hole, which could prevent proper seating of the screws, especially locking screws. Such plugs can be pre-inserted into the holes of the plates—only those, which need to be removed in order to insert the bone screws, are removed in surgery. Keeping other plugs in the holes has a benefit of increasing the strength of the plate. Protection of the holes during bending can be afforded by such hole plugs, which may be provided pre-installed in order to reduce surgery time. Screw hole plugs may then be left in place in the holes not used for bone screws.

The invention further relates to a construct comprising a plate according to the invention and at least one screw-hole plug. The construct may further comprise at least one locking screw or/and the construct may further comprise at least one standard bone screw.

The plate and the construct of the present invention are useful for the manufacture of a device for the treatment of bone fractures.

A method for the treatment of bone fractures comprises applying a plate of the present invention or a construct of the present invention to the fractured bone of a subject in need thereof.

The present invention relates in particular to a plate for treatment of bone fractures with reduced potential contact to bone through a combination of recesses of preferably approximately annular form surrounding at least some of the screw holes at the lower, bone facing surface of the plate, wherein the plate comprises transverse grooves between at least some of the holes. The plate allows for use of locking as well as conventional bone screws. With the transverse grooves cut into the plate from the lower surface and/or from the sides, the strength of the plate at the span between the holes is lower than at the screw holes. The plate can be bent in both planes without undue deformation of the screw holes. Protection of the holes during bending is afforded by hole plugs, which may be provided pre-installed in order to reduce surgery time. Screw hole plugs may then be left in place in the holes not used for bone screws.

The plate is suitable for application in human and in veterinary medicine.

LIST OF THE DRAWINGS

DETAILED DESCRIPTION OF THE INVENTION

Figure 1:
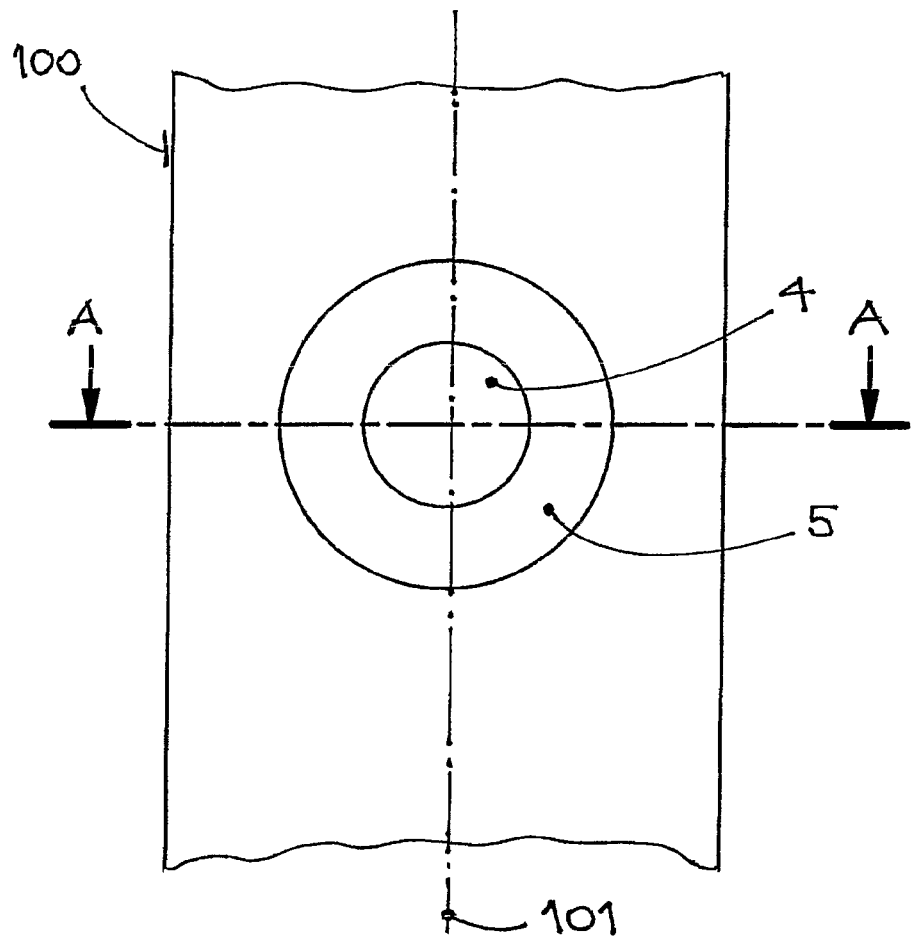
FIG. 1 shows a plate segment with a screw hole and a recess from the lower surface.
Figure 1:
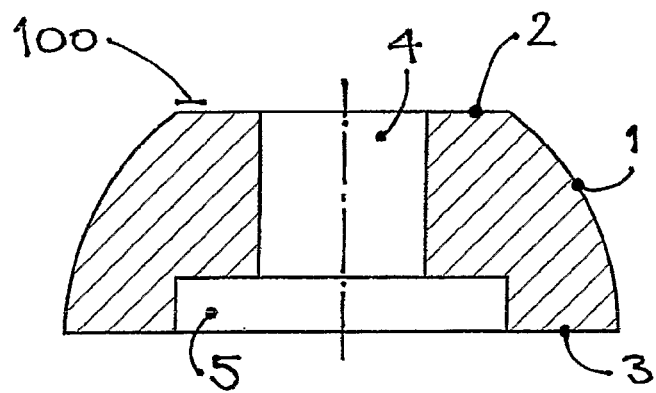

A section of the plate, 100, is shown in a normal projection from its lower, bone-facing surface, 3, on FIG. 1, together with a transverse cross section, A-A, cut through the screw hole, 4. The upper surface, 2, of the plate, 100, is parallel to the lower surface, 3, while the sides of the plate, 1, may be beneficially curved and inclined, so as to make the upper surface of the plate narrower in order to facilitate closure of the soft tissue over the plate. The screw hole, 4, is surrounded by a recess, 5, at the lower surface, 3, of the plate. The purpose of the recess, 5, is to eliminate the potential contact of the plate and the bone surrounding the screw. The lower surface, 3, of the plate, 100, is essentially planar.

Figure 2:
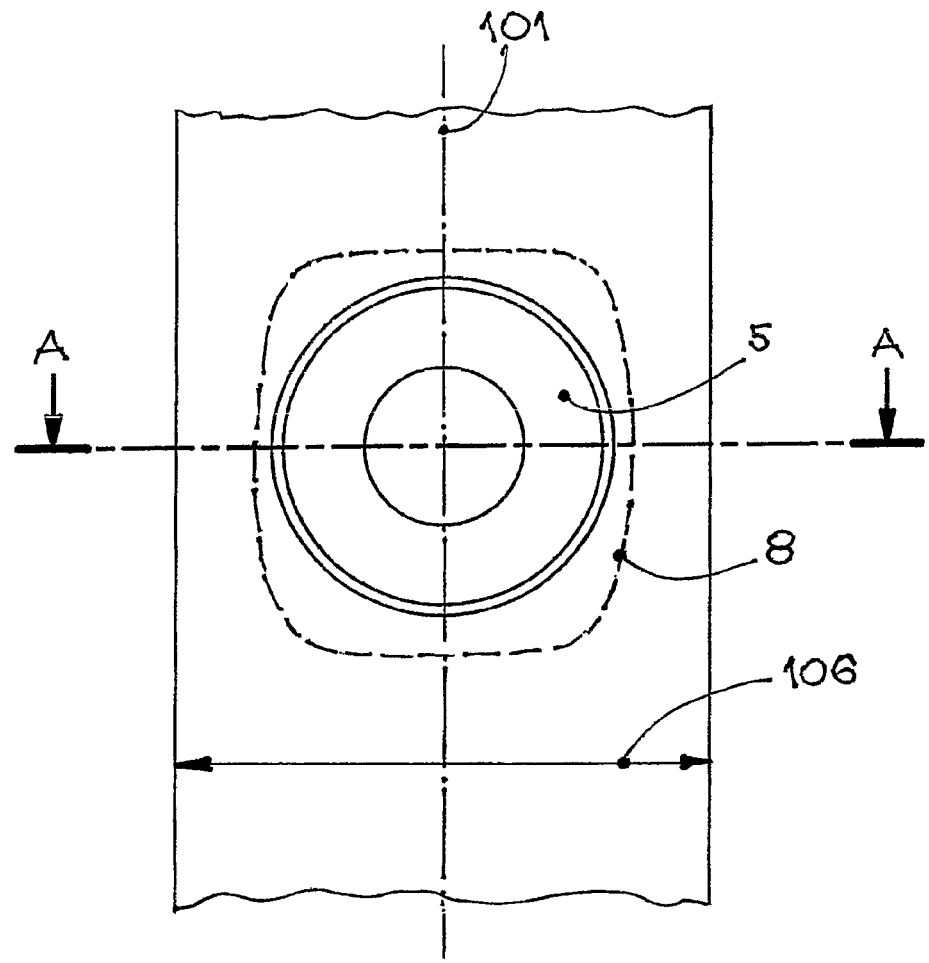
FIG. 2 shows a detail of the recess.
Figure 2:
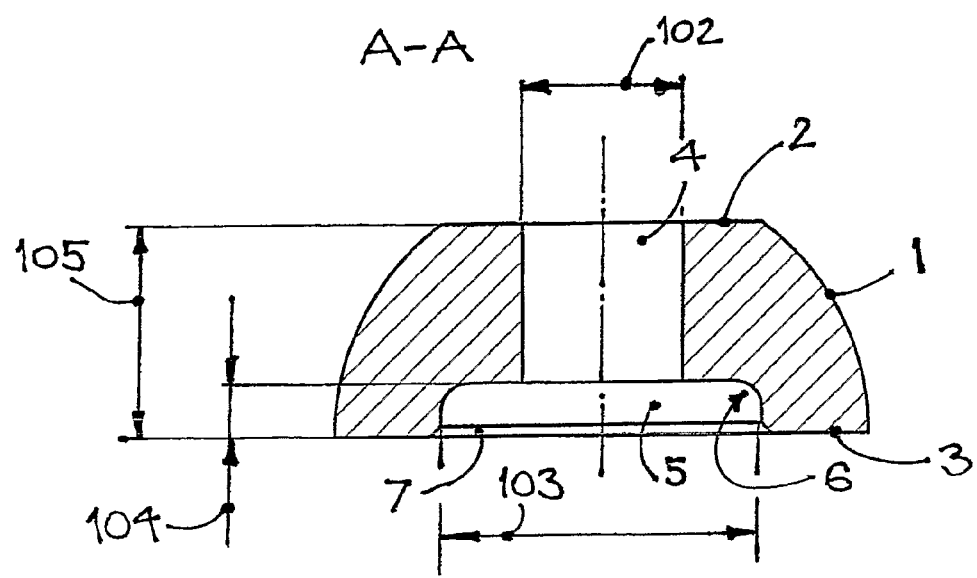

While the shape of the recess, 5, is shown as being circular in shape when viewed from the lower side of the plate, other shapes, such as that shown by dotted line, 8, on FIG. 2, can be used to achieve the same effect. A shape somewhat elongated in the direction of the long axis, 101, of the plate can be used to reduce the stresses at the transverse aspect of the plate along the remaining lower surface, 3. The recess can also be rounded, 6, at its base and/or faceted at its edge, 7, as one skilled in art would do to avoid stress concentrations at sharp corners, or injuries at sharp edges.

The diameter, 103, of the recess, 5, is significantly larger than the diameter, 102, of the hole 4 and smaller than the width, 106, of the plate. Preferably, to achieve good proportions of the screw and the plate, the width of the plate should be approximately 2.5 to 3.5 times larger than the diameter of the screw hole, and the recess diameter, 103, should be about 1.5 to 2 times larger than the diameter of the screw hole, 102. The depth, 104, of the recess, 5, should be scaled to the thickness, 105, of the plate; a good compromise between the need to provide a safe clearance to the bone and the need to maintain sufficient strength of the plate, suggests a preferred ratio of about 1 to 4, i.e. the depth of the recess should be about 25% of the plate thickness. In general, the depth of the recess may be about 20 to about 30% of the plate thickness.

Figure 3:
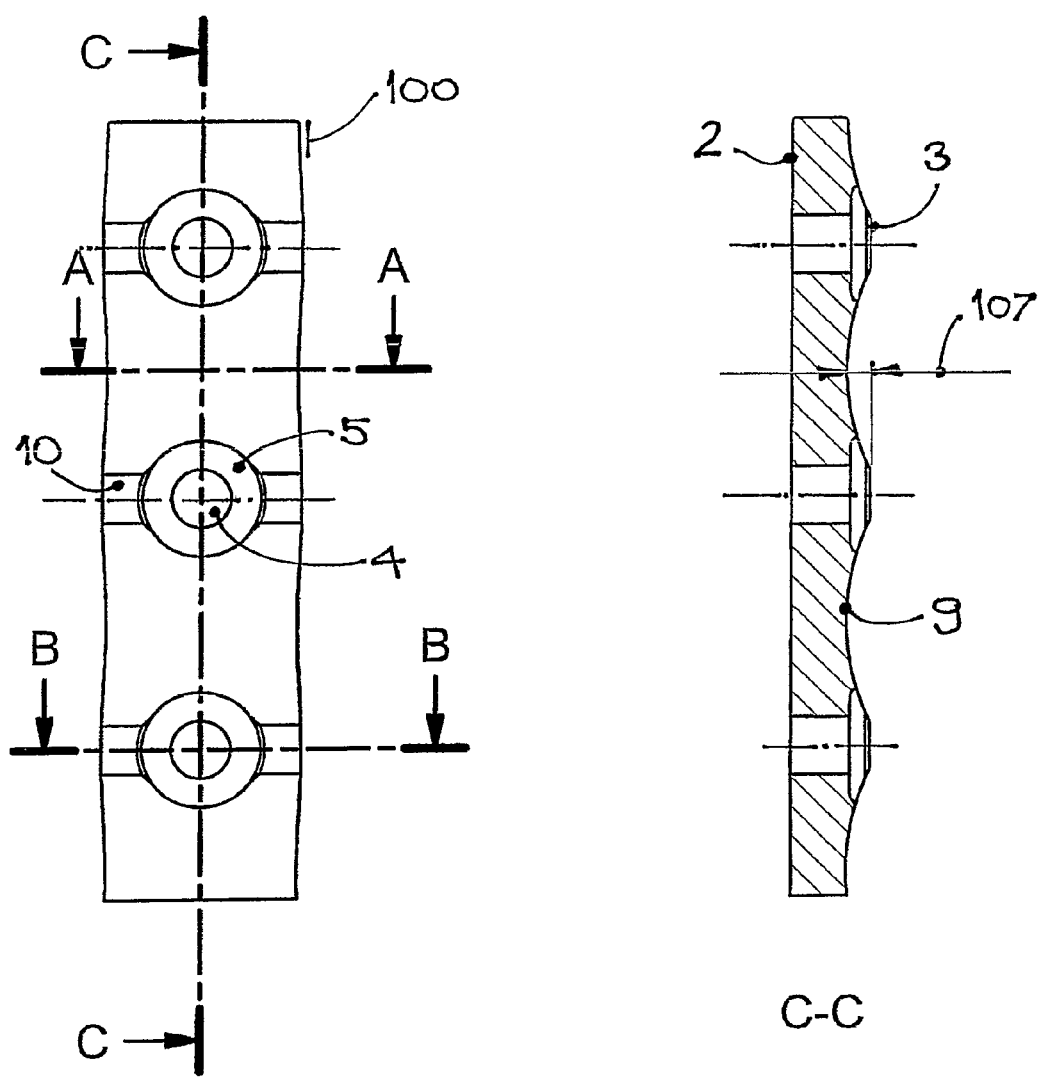
FIG. 3 shows a plate segment with 3 holes and transverse grooves.
Figure 3:
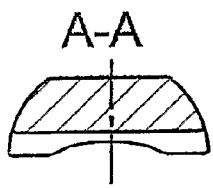
Figure 3:
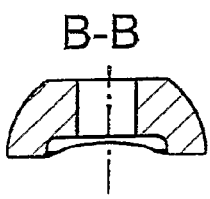

A further reduction of the potential contact between the plate and the bone is achieved by transverse grooves, 9, formed from the lower surface, 3, and positioned between the screw holes, 4, of the plate, 100, FIG. 3. The depth, 107, of the grooves, 9, is about the same, or slightly larger than the depth of recesses, 5. Transverse cross-sections through a hole, B-B, and between two holes, A-A, are also shown on FIG. 3. Note that the apparent arch-shaped section of the lower surface is in fact just the projection of the intersecting grooves, 9, and recesses, 5.

Figure 4:
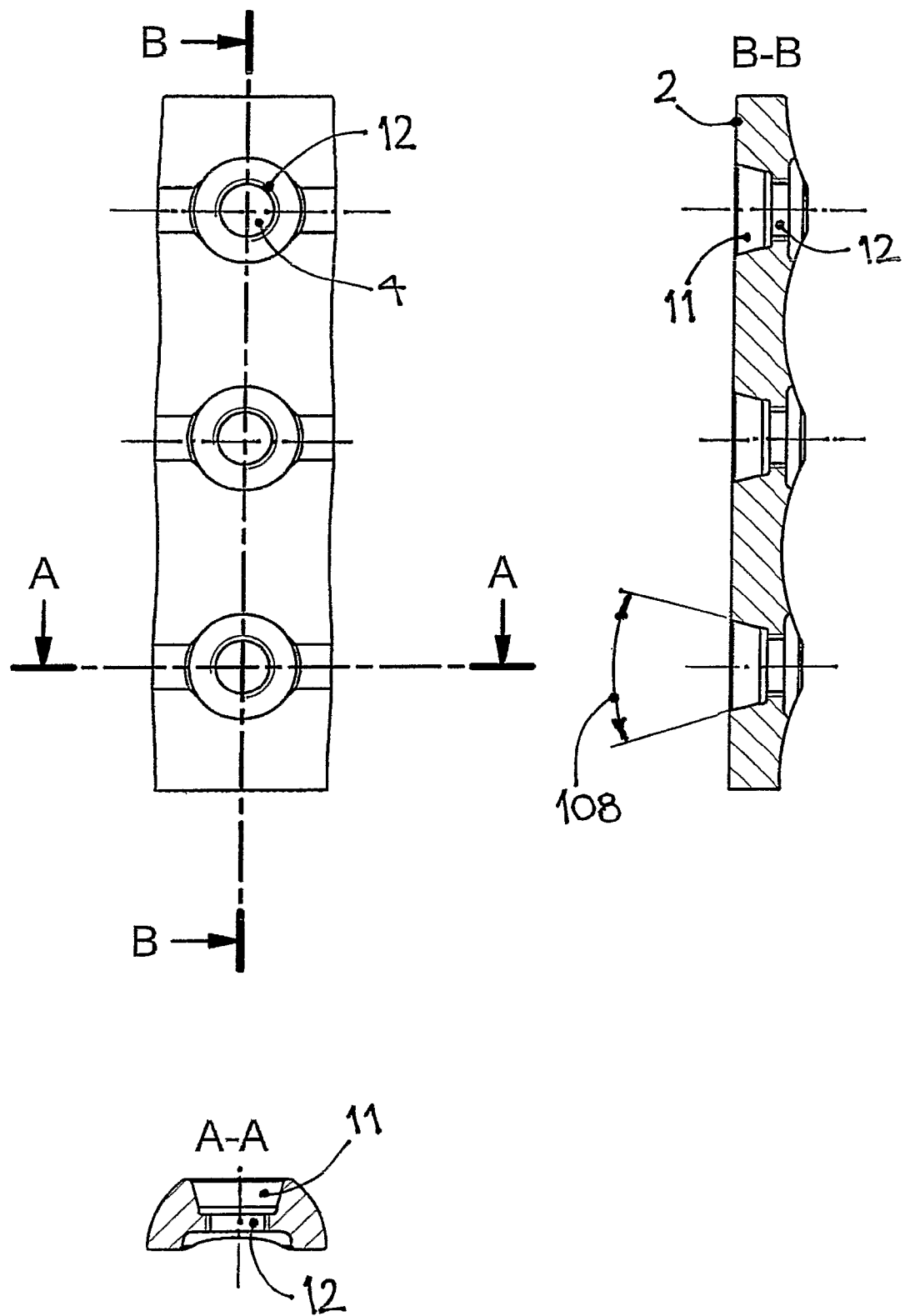
FIG. 4 shows a screw hole with a conical entry section from the upper surface and threads in the mid-lower section.

Preferred shape of the entry side, 11, of the screw holes, 4, is conical, FIG. 4. The angle of the cone, 108, should be large enough to prevent friction locking of the matching screw head, preferably about 25 degrees or more, more preferably about 30 degrees or more. Conical shape, 11, of the hole, 4, preferably reaches to about the mid plane of the plate—the remaining section of the hole, 4, is provided with threads, 12. These threads match the one and only thread of the locking screw.

Figure 5:
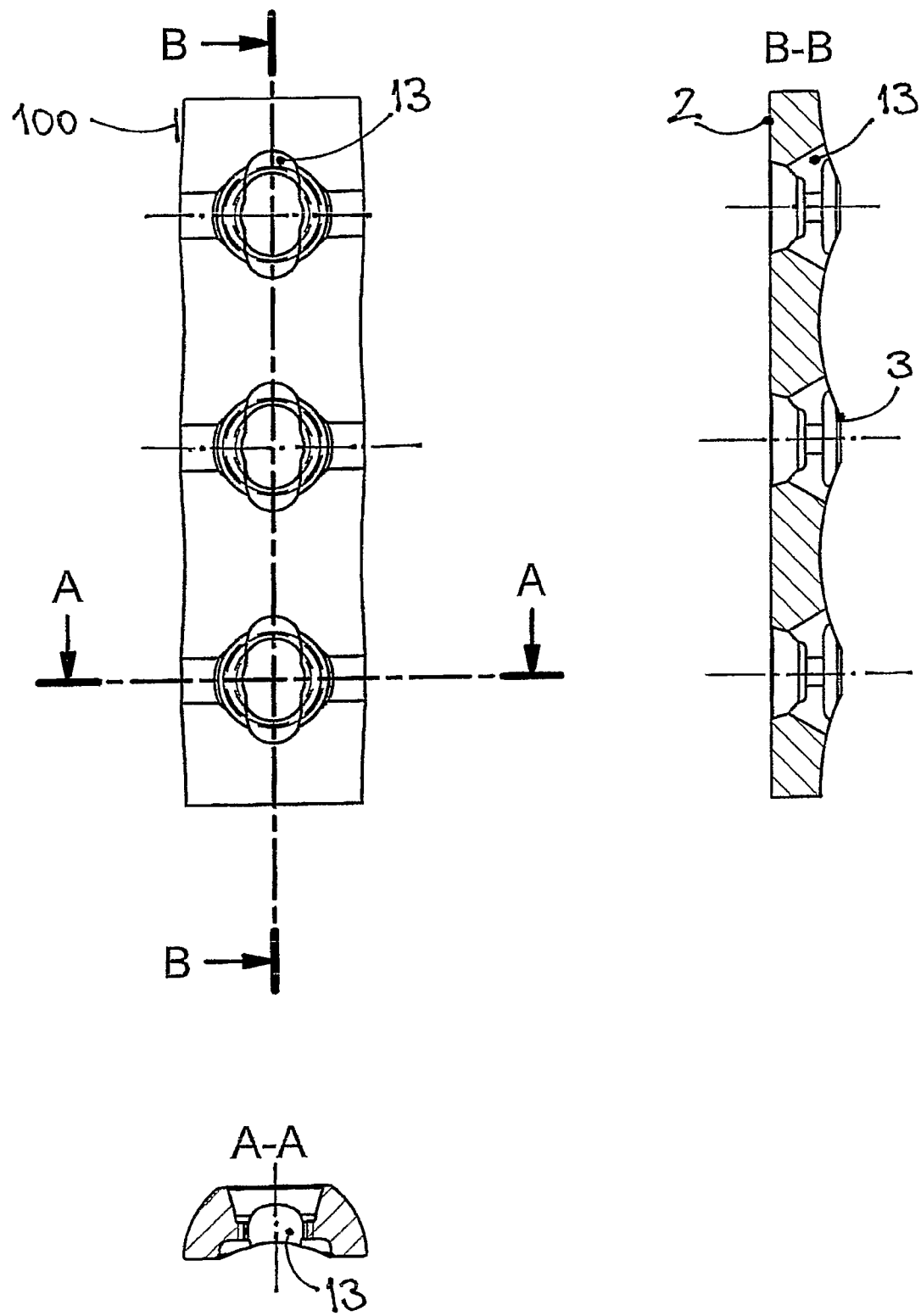
FIG. 5 shows a screw hole with angular release cuts from the lower surface.

To allow for use of conventional bone screws in conjunction with this plate, and to facilitate use of these screws for lagging bone fractures (compressing bones at the fracture by a fracture surface traversing screw), should that be elected by the surgeon, the exit side of the screw hole, 4, may be modified by angular release cuts, 13, FIG. 5.

Figure 6:
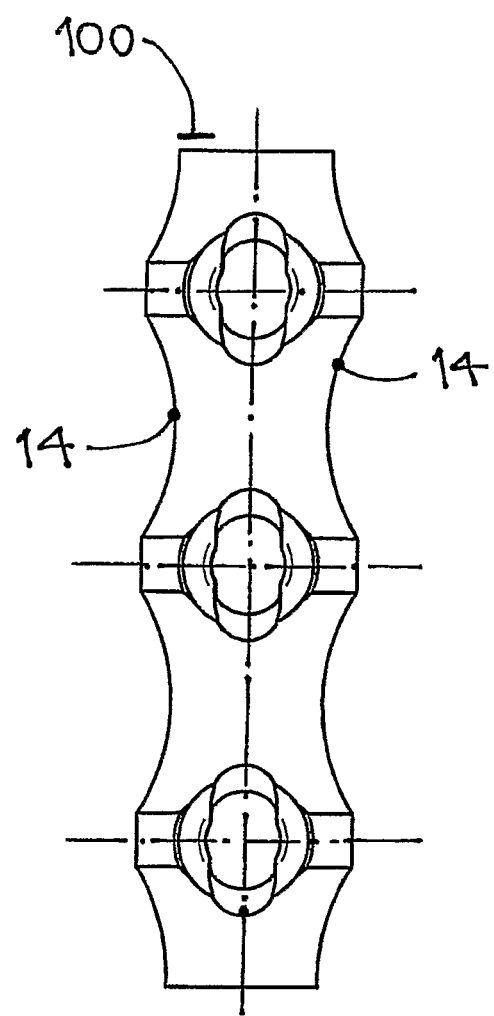
FIG. 6 shows a plate with side cuts between the holes.

In many uses of bone plates, it is desirable to bend the plate in both planes. So-called reconstruction plates with deep side cuts do exist, but those are intended for use in less loaded, complex bones, e.g. those of the pelvis. The plate disclosed here may be provided with side cuts, 14, FIG. 6, which allow for sufficient bending of the plate in both planes to match the shapes of the long bones, especially near joints. An important, further function of the side cuts 14, is to make the strength of the plate more uniform. This is beneficial not only for added ease of adaptation, but also for reducing the risk of plate breakage in functional use.

Figure 7:
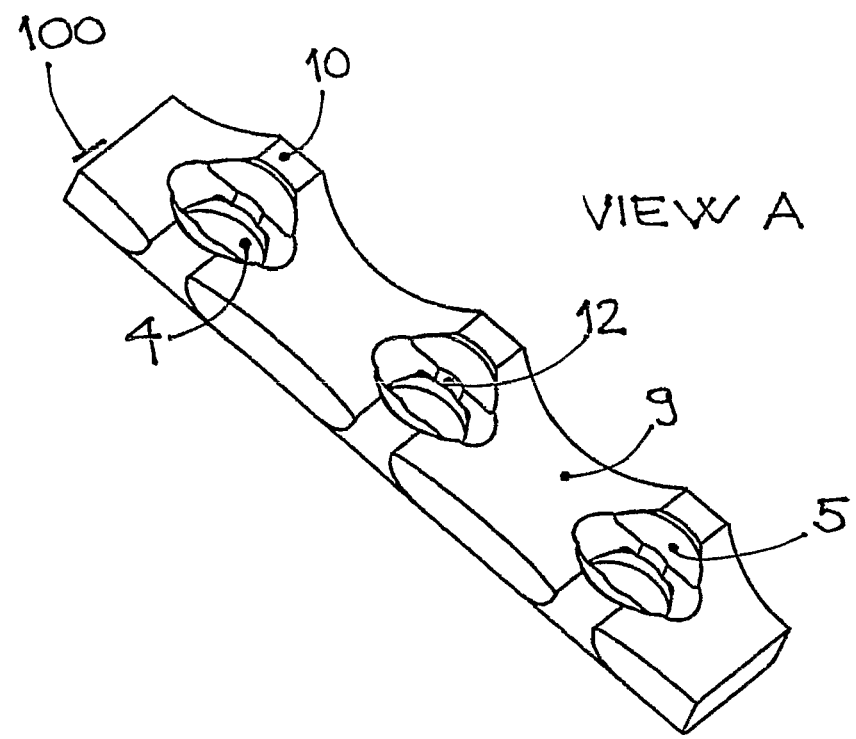
FIG. 7 shows a perspective view of the plate from below and from above.
Figure 7:
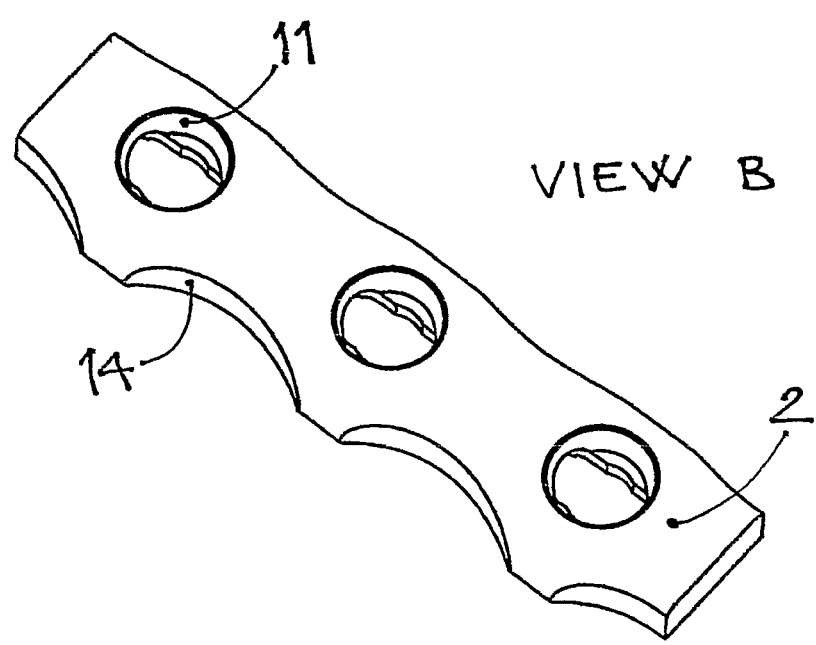

All innovative features of the plate, 100, are shown again in a perspective view A, from below, and a perspective view B from above, FIG. 7. Note that only two small areas, 10, per screw hole, 4, can potentially contact the bone the plate is placed upon.

Figure 8:
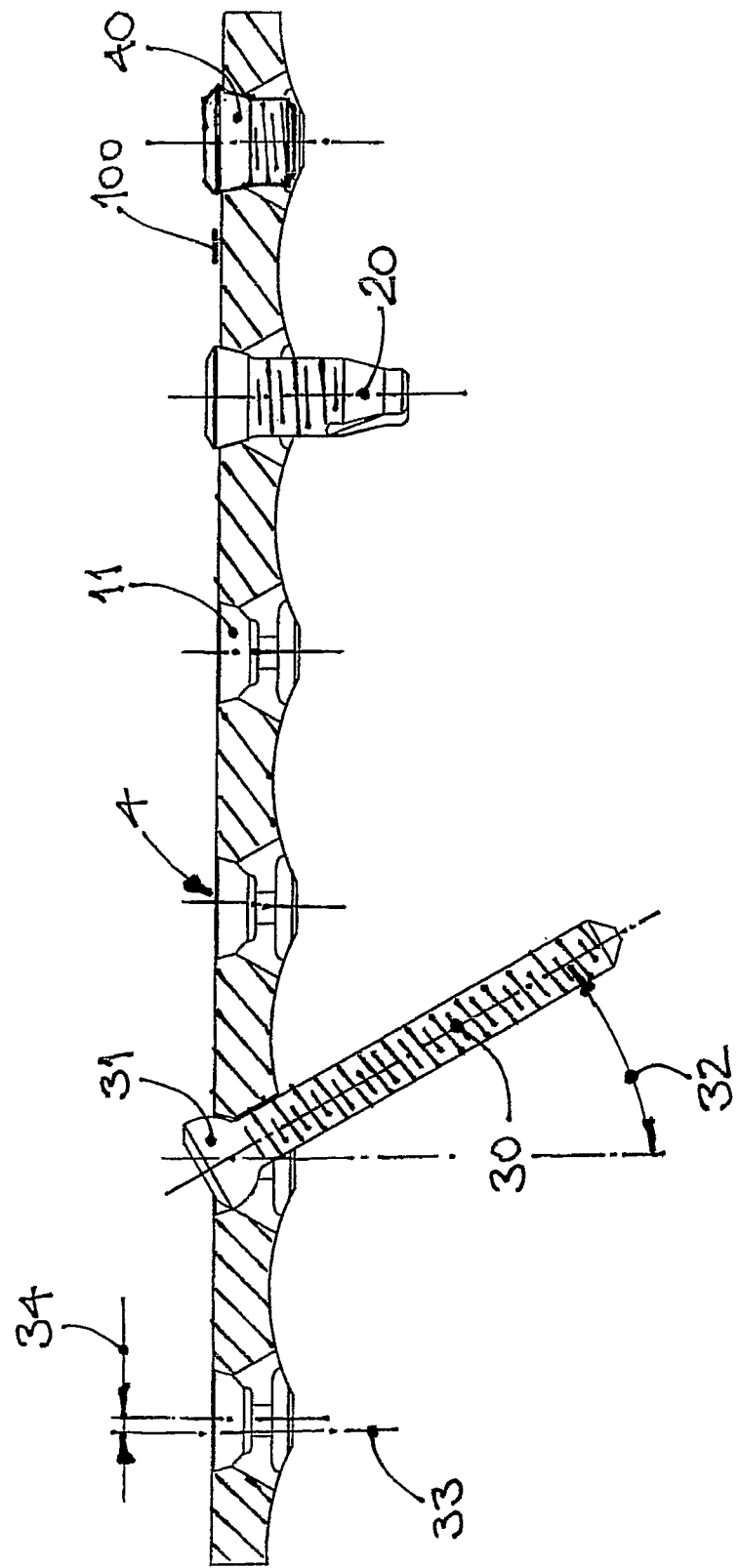
FIG. 8 shows a construct with a plate, a locking screw, a conventional screw and screw hole plug.

A construct of the plate, 100, and different screws is shown on FIG. 8. Preferred use of the plate, 100, for bone fracture treatment is with locking, short, screws, 20. However, conventional screws, 30, can also be used, especially if the fracture is near a joint where cortical bone is thin. Conventional screws have spherical heads, 31, which can be selected to just fit into the conical section 11 of the holes 4. In addition, the outside diameter of the conventional screw, 30, needs to be smaller than the core diameter of the locking screw, 20.

Angular releases, 13, allow for angulation, 32, of the screw 30. Should self-compression of the fracture by the screw insertion be desired, the pilot screw hole, 33, for a conventional screw can be drilled shifted by an amount, 34, from the centre of the hole. Driving a screw down will then cause a shift of the plate and the bone.

Screw holes, 4, can be plugged by plugs, 40, which, basically, are just short locking screws. Using such plugs, 40, in the plate holes, while adapting the plate to the bone by bending and torsion, reduces the risk of excessive deformation of the hole, which could prevent proper seating of the screws, especially locking screws, 20. Such plugs can be pre-inserted into the holes of the plates—only those, which need to be removed in order to insert the bone screws, are removed in surgery. Keeping other plugs in the holes has a benefit of increasing the strength of the plate.

Figure 9:
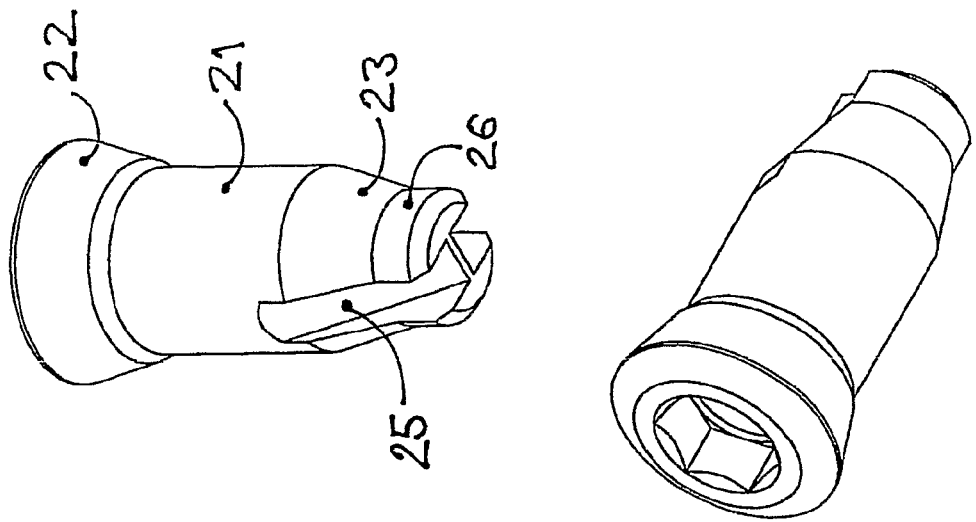
FIG. 9 shows a locking screw.
Figure 9:
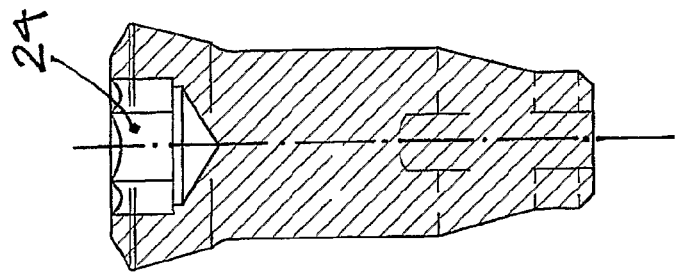
Figure 9:
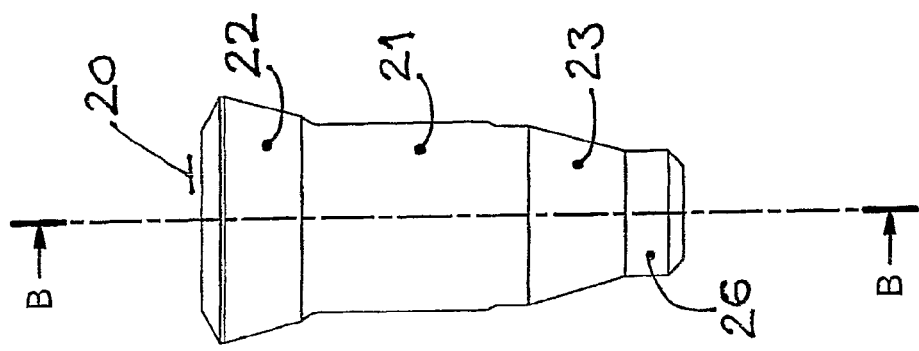

Locking screws, 20, are shown in normal projection, a cross-section and in perspective views on FIG. 9. The head, 22, of the screw is matching the screw hole entry section, 11; the body, 21, of the screw is threaded with the same threads as the screw hole, 12; the conical front section, 23, is provided with thread tapping recesses, 25; the very tip of the screw, 26, is cylindrical and helps to properly centre the screw. Screws are driven via screwdriver recess 24.

The invention claimed is:

1. A plate (100) for treating bone fractures having an upper surface (2) and a lower bone-facing surface (3) connecting opposite side edges of the plate, and at least two holes (4) for attachment to the bone extending from the upper surface (2) to the lower surface (3), wherein said holes are surrounded by recesses (5) recessed within the lower bone-facing surface (3), wherein arch shaped transverse grooves (9) are positioned between at least some of the holes (4) and extend from one of the opposite side edges to the other opposite side edge of the plate (100).

2. A plate according to claim 1, wherein the transverse grooves (9) further reduce the potential contact of the lower surface (3) of the plate and the bone, leaving intact only two small areas (10) of the lower surface (3) per said hole.

3. A plate according to claim 1, wherein the transverse grooves (9) span an area between the recesses (5) at the lower surface (3).

4. A plate according to claim 1, wherein the transverse grooves (9) at least partially overlap with a portion of the recesses (5) at the lower surface (3).

5. A plate according to claim 1, wherein the transverse grooves have a depth that is equal or larger than the depth of the recesses (5).

6. A plate according to claim 1, wherein said recesses are of approximately annular form.

7. A plate according to claim 1, wherein a width of said plate is approximately 2.5 to 3.5 times larger than a diameter (102) of said holes (4); and a diameter (103) of said recesses is approximately 1.5 to 2 times larger than the diameter (102) of said holes (4).

8. A plate according to claim 1, wherein the recesses (5) have a depth that is approximately one fourth of a thickness of said plate (105).

9. A plate according to claim 1 having a hole (4) in its upper section (11) adjacent to the upper surface (2), wherein the hole (4) in its upper section (11) adjacent to the upper surface (2) is conical in shape.

10. A plate according to claim 9, wherein the conical section (11) of the hole (4) has a cone angle (108) above.

11. A plate according to claim 9 having a mid-to-lower section (12) of the hole (4), wherein the mid-to-lower section (12) of the hole (4) is provided with threads.

12. A plate according to claim 1, further provided with angular release cuts (13) extending longitudinally with respect to the hole (4) in its mid-to-lower section.

13. A plate according to claim 1, wherein the geometry of said plate is further modified by side cuts (14) spaced between at least some of the holes (4) and merging the transverse grooves (9).

14. A plate according to claim 13 having a cross section between the holes and a cross section at the holes, wherein the cross section between the holes has lower moments of resistance than the cross section at the holes.

15. A construct comprising a plate according to claim 1 and at least one screw-hole plug (40).

16. A construct comprising a plate according to claim 1 and at least one locking screw (20).

17. A construct comprising a plate according to claim 1 and at least one standard bone screw (30).

18. A method for the treatment of bone fractures comprising applying a plate of claim 1 to the fractured bone of a subject in need thereof.

19. A construct comprising a construct according to claim 15 and at least one locking screw (20).

20. A construct comprising a construct according to claim 15 and at least one standard bone screw.

21. A method for the treatment of bone fractures comprising applying a construct of claim 15 to the fractured bone of a subject in need thereof.

* * * * *